US012765747B2

(12) United States Patent
Tsujimoto

(10) Patent No.: US 12,765,747 B2
(45) Date of Patent: Oct. 20, 2026

(54) MEDICAL IMAGE PROCESSING SYSTEM AND METHOD FOR OPERATING MEDICAL IMAGE PROCESSING SYSTEM

(71) Applicant: FUJIFILM Corporation, Tokyo (JP)

(72) Inventor: Takayuki Tsujimoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 578 days.

(21) Appl. No.: 17/937,266

(22) Filed: Sep. 30, 2022

(65) Prior Publication Data

US 2023/0029239 A1 Jan. 26, 2023

Related U.S. Application Data

(63) Continuation of application No. PCT/JP2021/008739, filed on Mar. 5, 2021.

(30) Foreign Application Priority Data

Apr. 2, 2020 (JP) ................................ 2020-066912

(51) Int. Cl.

| | |
|---|---|
| ***A61B 8/08*** | (2006.01) |
| ***A61B 1/00*** | (2006.01) |
| ***G06T 7/00*** | (2017.01) |

(52) U.S. Cl.

CPC ........ *A61B 1/00009* (2013.01); *G06T 7/0012* (2013.01); *G06T 2207/10068* (2013.01)

(58) Field of Classification Search

USPC ..... 128/915–916, 920, 922–925; 378/35–46, 378/62–63, 86–90; 382/100–107, (Continued)

(56) References Cited

U.S. PATENT DOCUMENTS

2007/0016016 A1* 1/2007 Haras .................... G06T 7/0012 600/407
2008/0262354 A1 10/2008 Yoshida et al.

(Continued)

FOREIGN PATENT DOCUMENTS

JP 2007-330764 A 12/2007
JP 2008-006188 A 1/2008

(Continued)

OTHER PUBLICATIONS

Arturo Calderon; Method for Identifying Region of Interest With Time in Medical Image Processing Apparatus and Medical Image Processing Apparatus; 2006 (Year: 2006).*

(Continued)

*Primary Examiner* — Marcellus J Augustin
(74) *Attorney, Agent, or Firm* — Studebaker Brackett PLLC

(57) ABSTRACT

An endoscope system sequentially acquires a plurality of endoscopic images by continuously imaging an observation target. A recognition processing unit detects, from the acquired endoscopic images, regions including a lesion portion as regions-of-interest. A recognition result correction unit corrects a position of the region-of-interest of the specific image by using a position of the region-of-interest of a previous image acquired before the specific image and a position of the region-of-interest of a subsequent image acquired after the specific image.

16 Claims, 8 Drawing Sheets

(58) Field of Classification Search
USPC .................................. 382/128–159, 190–224
See application file for complete search history.

(56) References Cited

U.S. PATENT DOCUMENTS

| | | | | |
|---|---|---|---|---|
| 2009/0279753 | A1 | 11/2009 | Sakaida | |
| 2010/0104167 | A1 | 4/2010 | Sakaguchi et al. | |
| 2010/0195887 | A1* | 8/2010 | Abe | A61B 8/08 600/443 |
| 2018/0310905 | A1* | 11/2018 | Yoshida | A61B 6/487 |
| 2018/0311795 | A1* | 11/2018 | Morton | B23Q 3/1546 |
| 2019/0370970 | A1* | 12/2019 | Kim | G06T 7/0016 |
| 2020/0129042 | A1 | 4/2020 | Takahashi et al. | |
| 2021/0361142 | A1* | 11/2021 | Kitamura | A61B 1/00006 |

FOREIGN PATENT DOCUMENTS

| | | | |
|---|---|---|---|
| JP | 2010-131371 | A | 6/2010 |
| JP | 2013-013569 | A | 1/2013 |
| JP | 5825886 | B2 | 12/2015 |
| WO | 2018/216617 | A1 | 11/2018 |
| WO | 2019/123986 | A1 | 6/2019 |
| WO | 2019/235195 | A1 | 12/2019 |

OTHER PUBLICATIONS

Saito Takaaki; Medical Image Processing Device, Endoscope System, Diagnosis Assistance Device, and Medical Operation Assistance Device; 2019 (Year: 2019).*

Kamon, Shumpei; Medical Image Processing System; 2020 (Year: 2020).*

Medical Image Processing Device, Endoscope System, Diagnosis Assistance Device, and Medical Operation Assistance Device (Year: 2019).*

Medical Image Processing System (Year: 2020).*

International Search Report issued in PCT/JP2021/008739; mailed May 18, 2021.

International Preliminary Report on Patentability (Chapter I) and Written Opinion of the International Searching Authority issued in PCT/JP2021/008739; issued Sep. 29, 2022.

An Office Action; "Notice of Reasons for Refusal," mailed by the Japanese Patent Office on Aug. 29, 2023, which corresponds to Japanese Patent Application No. 2022-511709 and is related to U.S. Appl. No. 17/937,266; with English language translation.

* cited by examiner

MEDICAL IMAGE PROCESSING SYSTEM AND METHOD FOR OPERATING MEDICAL IMAGE PROCESSING SYSTEM

CROSS-REFERENCE TO RELATED APPLICATIONS

This application is a Continuation of PCT International Application No. PCT/JP2021/008739 filed on 5 Mar. 2021, which claims priority under 35 U.S.C § 119(a) to Japanese Patent Application No. 2020-066912 filed on 2 Apr. 2020. The above application is hereby expressly incorporated by reference, in its entirety, into the present application.

BACKGROUND OF THE INVENTION

1. Field of the Invention

The present invention relates to a medical image processing system and a method for operating a medical image processing system.

2. Description of the Related Art

In a medical field, image diagnosis such as diagnosis of a disease of a patient and follow-up are performed by using medical images such as endoscopic images, X-ray images, computed tomography (CT) images, and magnetic resonance (MR) images. Based on such image diagnosis, a doctor or the like make a decision on a treatment policy.

In recent years, in the image diagnosis using medical images, a medical image processing apparatus performs recognition processing on regions-of-interest that should be carefully observed, such as lesions and tumors in organs. In particular, machine learning methods such as deep learning contribute to improving performance and efficiency of recognition processing.

On the other hand, a result of the recognition processing performed by the medical image processing apparatus is not always perfect. For this reason, JP5825886B discloses a method of calculating a feature amount of an image by performing recognition processing on each of a plurality of medical images which are sequentially acquired by continuous imaging, correcting the feature amount calculated in the recognition processing by using the medical images which are imaged before and after the image on which the recognition processing is performed, and performing the recognition processing again by using the corrected feature amount.

SUMMARY OF THE INVENTION

In JP5825886B, a more accurate recognition result can be obtained by performing correction of the feature amount and re-recognition processing. On the other hand, there is a problem that a processing load for obtaining a recognition result increases.

The present invention has been made in view of the above background, and an object of the present invention is to provide a medical image processing system and a method for operating a medical image processing system capable of obtaining a more accurate recognition result while reducing a processing load.

In order to achieve the above object, according to an aspect of the present invention, there is provided a medical image processing system including: a memory that stores a program instruction; and a processor configured to execute the program instruction, in which the processor is configured to sequentially acquire a plurality of medical images generated by continuously imaging an observation target, detect regions-of-interest from the medical images by performing recognition processing on each of the plurality of medical images, and correct position information of the region-of-interest detected by the recognition processing performed on a specific medical image among the plurality of medical images by using pieces of position information of the regions-of-interest detected by the recognition processing performed on medical images for comparison which are imaged at least one timing of timings before and after the specific medical image.

The correction may be performed in a case where validity of a result of the recognition processing is lower than a predetermined threshold value.

The correction may be performed in a case where an instruction by a user is input.

In the correction, a linear sum of the pieces of position information of the regions-of-interest of the medical images for comparison may be used.

In the correction, the position information of the region-of-interest which is located within a predetermined range from the region-of-interest of the specific medical image among the regions-of-interest of the medical images for comparison may be used.

The recognition processing may include determination processing of determining the region-of-interest.

In the correction, correction of a result of the determination may be performed.

In the correction of the result of the determination, the number of the medical images for comparison for each type of the result of the determination may be used.

In the recognition processing, a convolutional neural network may be used.

The medical image may be an image obtained from an endoscope.

Further, in order to achieve the above object, according to an aspect of the present invention, there is provided a method for operating a medical image processing system including a memory that stores a program instruction and a processor configured to execute the program instruction, the method including: sequentially acquiring, via the processor, a plurality of medical images generated by continuously imaging an observation target; detecting, via the processor, regions-of-interest from the medical images by performing recognition processing on each of the plurality of medical images; and correcting, via the processor, position information of the region-of-interest detected by the recognition processing performed on a specific medical image among the plurality of medical images by using pieces of position information of the regions-of-interest detected by the recognition processing performed on medical images for comparison which are imaged at least one timing of timings before and after the specific medical image.

According to the present invention, it is possible to provide a medical image processing system and a method for operating a medical image processing system capable of obtaining a more accurate recognition result while reducing a processing load.

DESCRIPTION OF THE PREFERRED EMBODIMENTS

First Embodiment

Figure 1:
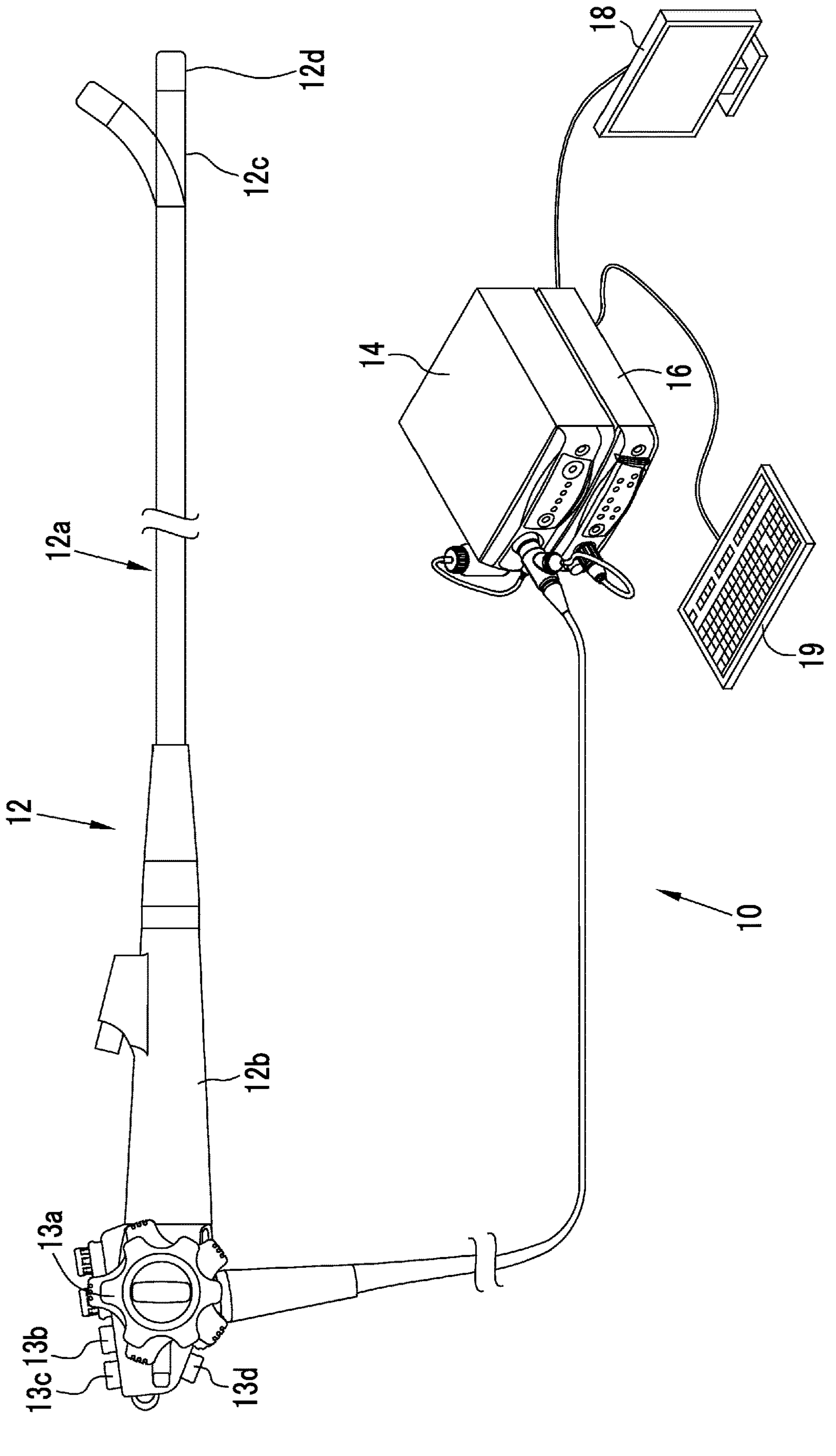
FIG. 1 is an external view of an endoscope system.

As illustrated in FIG. 1, an endoscope system 10 (medical image processing system) includes an endoscope 12, a light source device 14, a processor device 16, a monitor 18, and a console 19. The endoscope 12 is optically connected to the light source device 14, and is electrically connected to the processor device 16. The endoscope 12 includes an insertion part 12*a* to be inserted into a body of a subject, an operating part 12*b* provided at a proximal end portion of the insertion part 12*a*, and a bendable part 12*c* and a tip part 12*d* provided on a distal end side of the insertion part 12*a*. In a case where an angle knob 13*a* of the operating part 12*b* is operated, a bending operation of the bendable part 12*c* is performed. By the bending operation, the tip part 12*d* is directed in a desired direction.

In addition to the angle knob 13*a*, the operating part 12*b* includes a still image acquisition unit 13*b* used for a still image acquisition operation, a mode switching unit 13*c* used for an observation mode switching operation, and a zoom operating part 13*d* used for a zoom magnification changing operation. The still image acquisition unit 13*b* can perform a freeze operation for displaying a still image of an observation target on the monitor 18 and a release operation for saving the still image in a storage.

The endoscope system 10 has a normal mode, a special mode, and a region-of-interest mode as observation modes. In a case where the observation mode is the normal mode, a normal light beam obtained by combining light beams having a plurality of colors at a light quantity ratio for the normal mode Lc is emitted. Further, in a case where the observation mode is the special mode, a special light beam obtained by combining light beams having a plurality of colors at a light quantity ratio for the special mode Ls is emitted.

Further, in a case where the observation mode is the region-of-interest mode, an illumination light beam for the region-of-interest mode is emitted. In the present embodiment, as the illumination light beam for the region-of-interest mode, the normal light beam is emitted. On the other hand, the special light beam may be emitted.

The processor device 16 is electrically connected to the monitor 18 and the console 19. The monitor 18 outputs and displays an image of the observation target, information related to the image, and the like. The console 19 functions as a user interface that receives input operations such as designation of a region-of-interest (ROI), designation of an image on which recognition processing is to be performed, designation of an image on which recognition result correction processing is to be performed, designation of a recognition processing result, and function setting.

Figure 2:
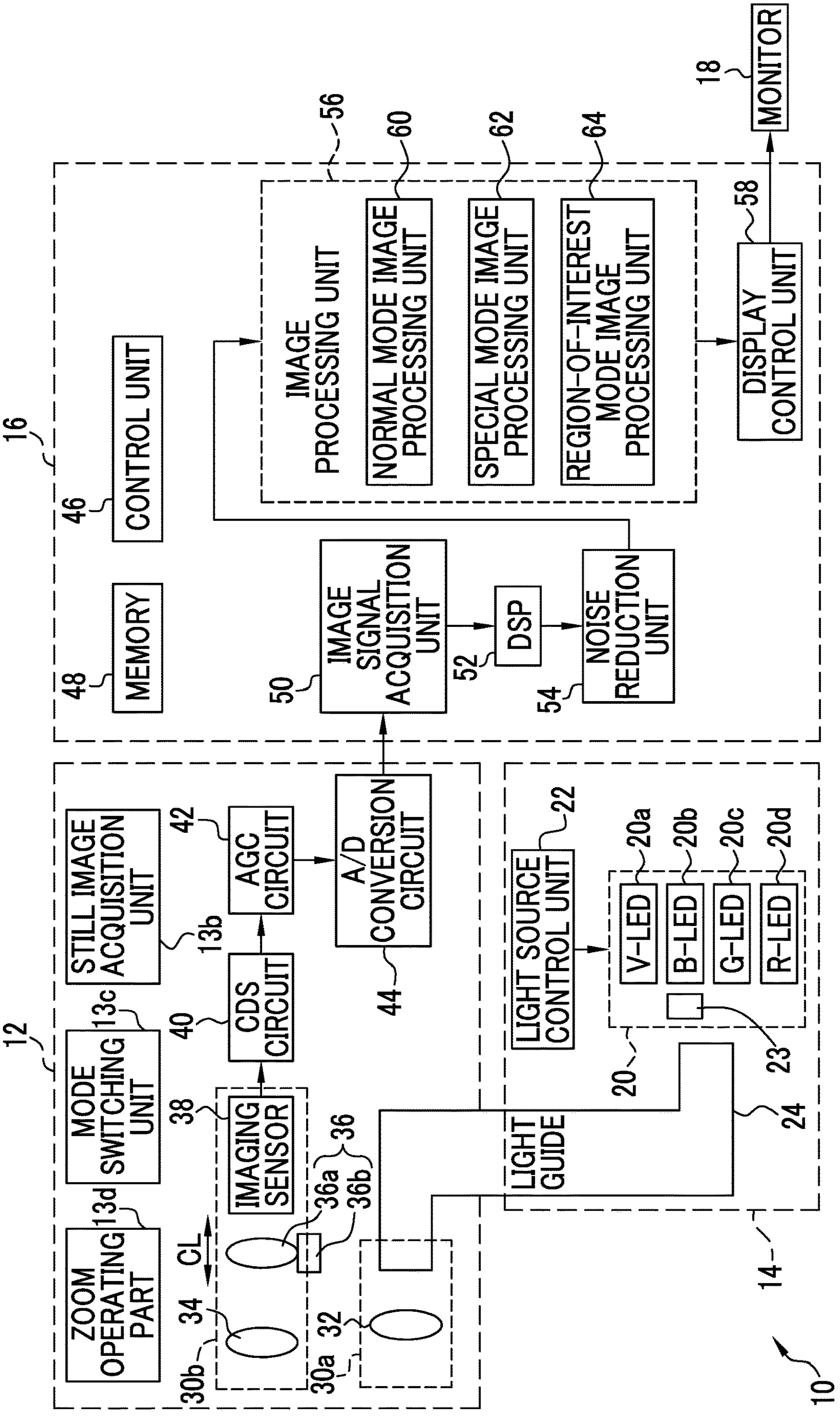
FIG. 2 is a block diagram illustrating a function of the endoscope system.

As illustrated in FIG. 2, the light source device 14 includes a light source unit 20 that emits an illumination light beam used for illuminating an observation target, and a light source control unit 22 that controls the light source unit 20. The light source unit 20 is a semiconductor light source such as a light emitting diode (LED) which emits light beams having a plurality of colors. The light source control unit 22 controls a light emission amount of the illumination light beams by turning ON/OFF the LEDs or adjusting a drive current or a drive voltage of the LEDs. Further, the light source control unit 22 controls a wavelength band of the illumination light beams by changing an optical filter or the like.

Figure 3:
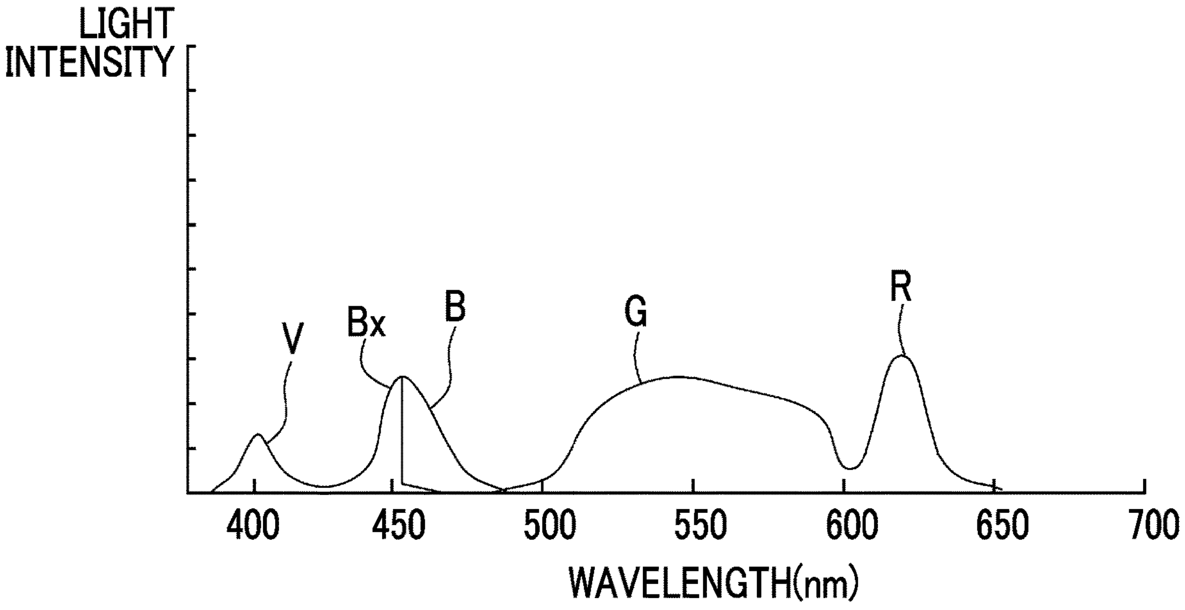
FIG. 3 is a graph illustrating spectral spectra of a violet light beam V, a blue light beam B, a blue light beam Bx, a green light beam G, and a red light beam R.

In the first embodiment, the light source unit 20 includes four-color LEDs of a violet light emitting diode (V-LED) 20*a*, a blue light emitting diode (B-LED) 20*b*, a green light emitting diode (G-LED) 20*c*, and a red light emitting diode (R-LED) 20*d* and a wavelength cut filter 23. As illustrated in FIG. 3, the V-LED 20*a* emits a violet light beam V in a wavelength band of 380 nm to 420 nm.

The B-LED 20*b* emits a blue light beam B in a wavelength band of 420 nm to 500 nm. In the blue light beams B emitted from the B-LED 23*b*, at least a light beam having a wavelength longer than a peak wavelength of 450 nm is cut by the wavelength cut filter 23. Thereby, the blue light beam Bx passing through the wavelength cut filter 23 is within a wavelength range of 420 to 460 nm. The reason why the light beam in a wavelength band including wavelengths longer than 460 nm is cut in this way is that the light beam in a wavelength band including wavelengths longer than 460 nm causes a decrease in vascular contrast of a blood vessel as an observation target. The wavelength cut filter 23 may dim the light beam in a wavelength band including wavelengths longer than 460 nm instead of cutting the light beam in a wavelength band including wavelengths longer than 460 nm.

The G-LED 20*c* emits a green light beam G in a wavelength band of 480 nm to 600 nm. The R-LED 20*d* emits a red light beam R in a wavelength band of 600 nm to 650 nm. In the light beams emitted from the LEDs 20*a* to 20*d*, central wavelengths and peak wavelengths may be the same, or may be different from each other.

The light source control unit 22 adjusts a light emission timing, a light emission period, a light emission amount, and a spectral spectrum of the illumination light beams by independently controlling ON/OFF of each of the LEDs 20*a* to 20*d*, a light emission amount of each of the LEDs in an ON state, or the like. The light source control unit 22 controls ON/OFF of the LEDs depending on the observation mode. The reference brightness can be set by a brightness setting unit of the light source device 14, the console 19, or the like.

Figure 4:
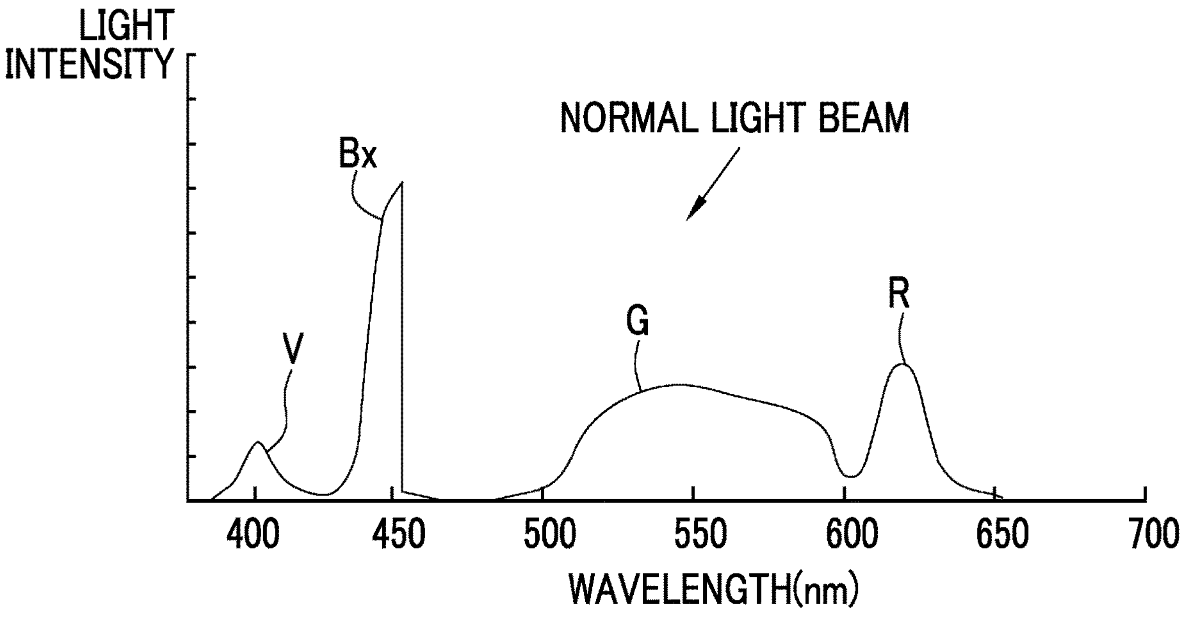
FIG. 4 is a graph illustrating a spectral spectrum of a normal light beam.

In a case of the normal mode or the region-of-interest mode, the light source control unit 22 turns on all the V-LED 20*a*, the B-LED 20*b*, the G-LED 20*c*, and the R-LED 20*d*. At that time, as illustrated in FIG. 4, a light quantity ratio Lc between the violet light beam V, the blue light beam B, the green light beam G, and the red light beam R is set such that a peak of a light intensity of the blue light beam Bx is higher than a peak of a light intensity of any one of the violet light beam V, the green light beam GC and the red light beam R. Thereby, in the normal mode or the region-of-interest mode, the light beams for the normal mode or the region-of-interest mode that have the plurality of colors and include the violet light beam V, the blue light beam Bx, the green light beam G and the red light beam R are emitted from the light source device 14, as the normal light beams. The normal light beam is almost white because the normal light beam has an intensity of a certain level or higher from a blue wavelength band to a red wavelength band.

Figure 5:
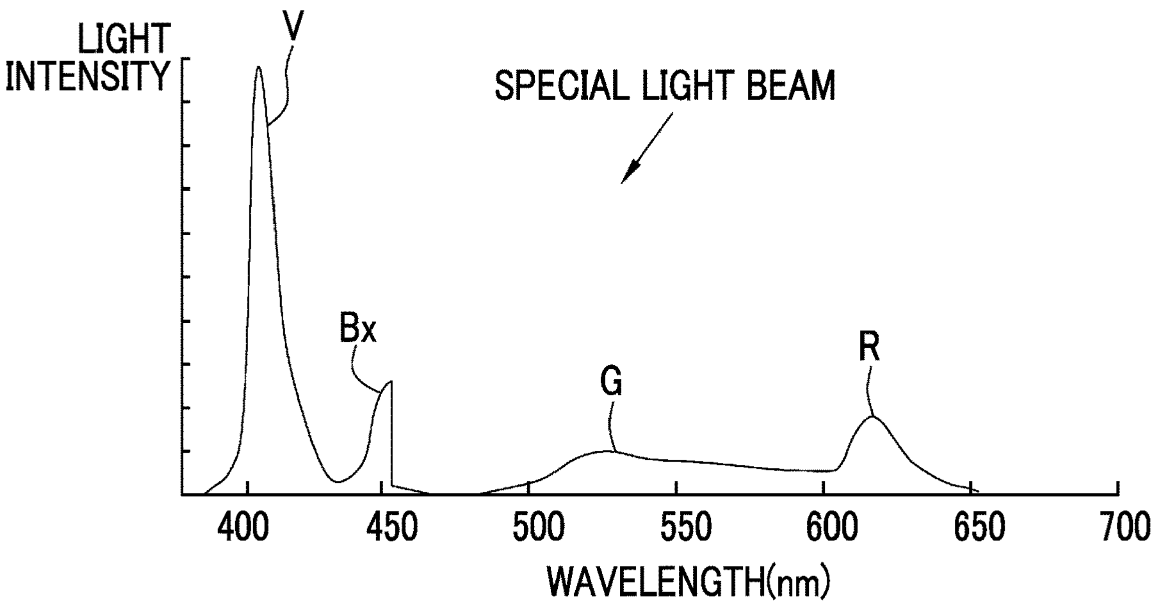
FIG. 5 is a graph illustrating a spectral spectrum of a special light beam.

In a case of the special mode, the light source control unit 22 turns on all the V-LED 20*a*, the B-LED 20*b*, the G-LED 20*c*, and the R-LED 20*d*. At that time, as illustrated in FIG. 5, a light quantity ratio Ls between the violet light beam V, the blue light beam B, the green light beam G, and the red light beam R is set such that a peak of a light intensity of the violet light beam V is higher than a peak of a light intensity of any one of the blue light beam Bx, the green light beam G, and the red light beam R. Further, the peaks of the light intensities of the green light beam G and the red light beam R are set to be lower than the peaks of the light intensities of the violet light beam V and the blue light beam Bx. Thereby, in the special mode, the light beams for the special mode that have the plurality of colors and include the violet light beam V, the blue light beam Bx, the green light beam G, and the red light beam R are emitted from the light source device 14, as the special light beams. The special light beam is bluish because a proportion of the violet light beams V is high. The special light beam may not include light beams having all four colors, and may include at least a light beam from a one-color LED among the four-color LEDs 20*a* to 20*d*. Further, preferably, the special light beam has a main wavelength band, for example, a peak wavelength or a central wavelength within a range of 450 nm or lower.

Returning to FIG. 2, the illumination light beam emitted by the light source unit 20 enters into a light guide 24 inserted into the insertion part 12*a* via an optical path coupling unit (not illustrated) formed by a mirror, a lens, and the like. The light guide 24 is incorporated in the endoscope 12 and the universal cord, and propagates the illumination light beam to the tip part 12*d* of the endoscope 12. The universal cord is a cord that connects the endoscope 12, the light source device 14, and the processor device 16. As the light guide 24, a multi-mode fiber can be used. As an example, for the light guide 24, a fine fiber cable having a core diameter of 105 μm, a clad diameter of 125 μm, and a diameter of φ0.3 mm to φ0.5 mm including a protective layer serving as an outer skin can be used.

An illumination optical system 30*a* and an imaging optical system 30*b* are provided at the tip part 12*d* of the endoscope 12. The illumination optical system 30*a* includes an illumination lens 32. The observation target is illuminated with the illumination light beam propagating through the light guide 24 via the illumination lens 32. The imaging optical system 30*b* includes an objective lens 34, a magnification optical system 36, and an imaging sensor 38. Various light beams such as a reflected light beam, a scattered light beam, and a fluorescent light beam from the observation target enter into the imaging sensor 38 via the objective lens 34 and the magnification optical system 36. Thereby, an image of the observation target is formed on the imaging sensor 38.

The magnification optical system 36 includes a zoom lens 36*a* that magnifies the observation target and a lens driving unit 36*b* that moves the zoom lens 36*a* in an optical axis direction CL. The zoom lens 36*a* is freely moved between a telephoto end and a wide end according to zoom control by the lens driving unit 36*b*. Thereby, the observation target imaged on the imaging sensor 38 is magnified or reduced.

The imaging sensor 38 is a color imaging sensor that images the observation target irradiated with the illumination light beam. For each pixel of the imaging sensor 38, any one of an R (red) color filter, a G (green) color filter, and a B (blue) color filter is provided. The imaging sensor 38 receives light beams including a violet light beam to a blue light beam from a B pixel for which the B color filter is provided, receives a green light beam from a G pixel for which the G color filter is provided, and receives a red light beam from an R pixel for which the R color filter is provided. Then, an image signal of each of RGB colors is output from each color pixel. The imaging sensor 38 transmits the output image signal to a CDS circuit 40.

In the normal mode or the region-of-interest mode, the imaging sensor 38 outputs a Bc image signal from the B pixel, outputs a Gc image signal from the G pixel, and outputs an Rc image signal from the R pixel by imaging the observation target illuminated with the normal light beam. Further, in the special mode, the imaging sensor 38 outputs a Bs image signal from the B pixel, outputs a Gs image signal from the G pixel, and outputs an Rs image signal from the R pixel by imaging the observation target illuminated with the special light beam.

As the imaging sensor 38, a charge coupled device (CCD) imaging sensor, a complementary metal-oxide semiconductor (CMOS) imaging sensor, or the like can be used. Further, instead of the imaging sensor 38 provided with RGB primary color filters, a complementary color imaging sensor provided with complementary color filters for C (cyan), M (magenta), Y (yellow) and G (green) may be used. In a case where a complementary color imaging sensor is used, image signals of four colors of CMYG are output. Thus, by converting the image signals of four colors of CMYG into image signals of three colors of RGB by complementary-color-to-primary-color conversion, an image signal of each of RGB colors can be obtained as in the imaging sensor 38. Further, instead of the imaging sensor 38, a monochrome sensor without a color filter may be used.

The CDS circuit 40 performs correlated double sampling (CDS) on the analog image signal received from the imaging sensor 38. The image signal that passes through the CDS circuit 40 is input to an AGC circuit 42. The AGC circuit 42 performs automatic gain control (AGC) on the input image signal. An analog to digital (A/D) conversion circuit 44 converts the analog image signal that passes through the AGC circuit 42 into a digital image signal. The A/D conversion circuit 44 inputs the digital image signal after the A/D conversion to the processor device 16.

As illustrated in FIG. 2, the processor device 16 includes a control unit 46 that configures a processor of the present invention. The control unit 46 is a hardware resource for executing a program instruction stored in a memory 48, and executes the program instruction by driving and controlling each unit of the endoscope system 10. In a case where the control unit 46 drives and controls each unit of the endoscope system 10 according to the execution of the program instruction, the processor device 16 functions as an image signal acquisition unit 50, a digital signal processor (DSP) 52, a noise reduction unit 54, an image processing unit 56, and a display control unit 58.

The image signal acquisition unit 50 performs imaging by driving and controlling the endoscope 12 (imaging sensor 38 and the like), and acquires an endoscopic image (medical image). The image signal acquisition unit 50 sequentially acquires a plurality of endoscopic images by continuously imaging the observation target. The image signal acquisition unit 50 acquires an endoscopic image as a digital image signal corresponding to the observation mode. Specifically, in a case of the normal mode or the region-of-interest mode, a Bc image signal, a Gc image signal, and an Rc image signal are acquired. In a case of the special mode, a Bs image signal, a Gs image signal, and an Rs image signal are acquired. In a case of the region-of-interest mode, when the observation target is illuminated with the normal light beam, a Bc image signal, a Gc image signal, and an Rc image signal for one frame are acquired, and when the observation target is illuminated with the special light beam, a Bs image signal, a Gs image signal, and an Rs image signal for one frame are acquired.

The DSP 52 performs various signal processing such as defect correction processing, offset processing, DSP gain correction processing, linear matrix processing, gamma conversion processing, and demosaicing processing on the image signal acquired by the image signal acquisition unit 50. The defect correction processing corrects a signal of a defective pixel of the imaging sensor 38. The offset processing sets an accurate zero level by removing a dark current component from the image signal after the defect correction processing. The DSP gain correction processing adjusts a signal level by multiplying the image signal after the offset processing by a specific DSP gain.

The linear matrix processing enhances a color reproducibility of the image signal after the DSP gain correction processing. The gamma conversion processing adjusts brightness and chroma saturation of the image signal after the linear matrix processing. The demosaicing processing (also referred to as isotropic processing or synchronization processing) is performed on the image signal after the gamma conversion processing, and thus a signal of a color which is insufficient in each pixel is generated by interpolation. By the demosaicing processing, all the pixels have signals of each color of RGB colors. The noise reduction unit 54 reduces noise by performing noise reduction processing by, for example, a movement average method, a median filter method, or the like on the image signal after the demosaicing processing and the like by the DSP 52. The image signal after the noise reduction is input to the image processing unit 56.

The image processing unit 56 includes a normal mode image processing unit 60, a special mode image processing unit 62, and a region-of-interest mode image processing unit 64. The normal mode image processing unit 60 operates in a case where the normal mode is set, and performs color conversion processing, color enhancement processing, and structure enhancement processing on the Bc image signal, the Gc image signal, and the Rc image signal which are received. In the color conversion processing, color conversion processing including 3×3 matrix processing, gradation transformation processing, three-dimensional look up table (LUT) processing, and the like is performed on the RGB image signal.

The color enhancement processing is performed on the RGB image signal after the color conversion processing. The structure enhancement processing is processing for enhancing a structure of the observation target, and is performed on the RGB image signal after the color enhancement processing. A normal image can be obtained by performing various image processing and the like as described above. Since the normal image is an image obtained based on the normal light beam in which the violet light beam V, the blue light beam Bx, the green light beam G, and the red light beam R are well balanced, the normal image has a natural hue.

The special mode image processing unit 62 operates in a case where the special mode is set. The special mode image processing unit 62 performs color conversion processing, color enhancement processing, and structure enhancement processing on the Bs image signal, the Gs image signal, and the Rs image signal which are received. The processing contents of the color conversion processing, the color enhancement processing, and the structure enhancement processing are the same as the processing contents in the normal mode image processing unit 60. A special image can be obtained by performing various image processing as described above. The special image is an image obtained based on the special light beam in which the light emission amount of the violet light beam V is larger than the light emission amounts of the blue light beam Bx, the green light beam G, and the red light beam R of other colors, the violet light beam having a high absorption coefficient of hemoglobin in a blood vessel. Thus, a resolution of a vascular structure or a ductal structure is higher than a resolution of another structure.

The region-of-interest mode image processing unit 64 operates in a case where the region-of-interest mode is set. The region-of-interest mode image processing unit 64 performs the same image processing as the processing in the normal mode image processing unit 60, such as color conversion processing, on the Bc image signal, the Gc image signal, and the Rc image signal which are received.

Figure 6:
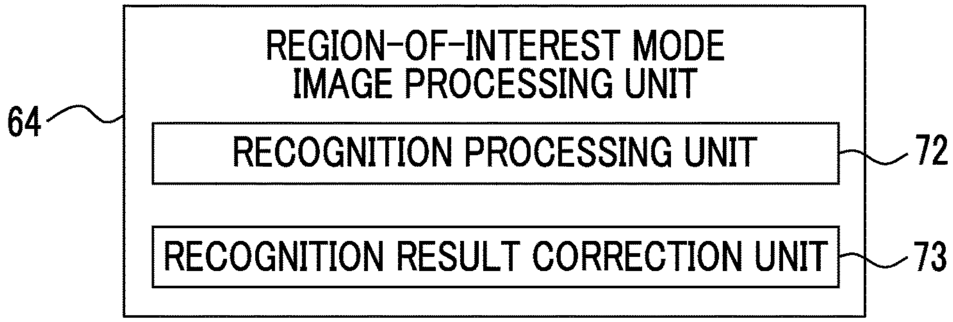
FIG. 6 is a block diagram illustrating a function of a region-of-interest mode image processing unit.
Figure 7:
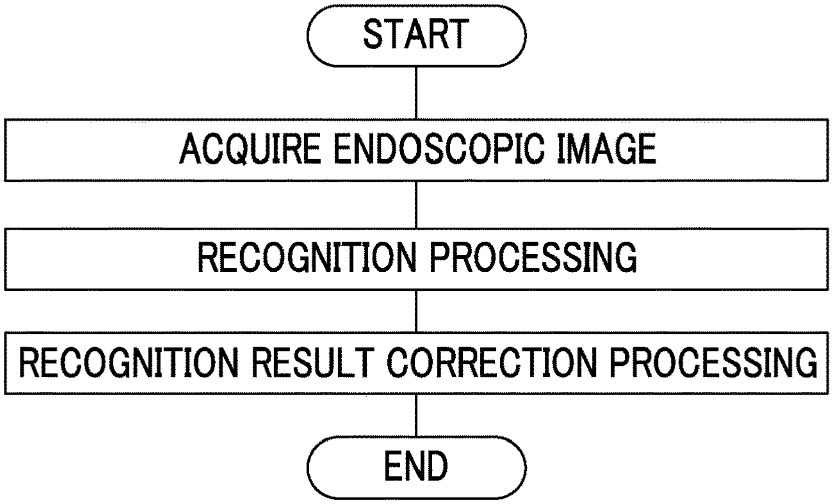
FIG. 7 is a flowchart illustrating a series of flows of a region-of-interest mode.

As illustrated in FIG. 6, the region-of-interest mode image processing unit 64 functions as a recognition processing unit 72 and a recognition result correction unit 73 by driving and controlling of the control unit 46 (refer to FIG. 2) according to an execution of the program instruction described above. As illustrated in FIG. 7, the recognition processing unit 72 sequentially acquires endoscopic images by the same image processing as the processing in the normal mode image processing unit 60, analyzes the acquired endoscopic images, and performs recognition processing. The recognition processing performed by the recognition processing unit 72 includes detection processing for detecting a region-of-interest from a recognition image (in the present embodiment, endoscopic image) and determination processing for determining a type of a lesion included in the recognition image. Further, the determination processing includes processing performed on the region-of-interest and processing performed on the entire recognition image. In the present embodiment, the recognition processing unit 72 performs detection processing for detecting, as a region-of-interest, a rectangular region including a lesion portion from an endoscopic image.

In the recognition processing, the recognition processing unit 72 first divides the endoscopic image into a plurality of small regions, for example, square regions for the number of pixels. Next, an image feature amount is calculated from the divided endoscopic image. Subsequently, based on the calculated feature amount, whether or not each small region is a lesion portion is determined. Finally, a group of small regions identified as the same type is extracted as one lesion portion, and a rectangular region including the extracted lesion portion is detected as a region-of-interest. As the determination method described above, preferably, a machine learning algorithm such as a convolutional neural network or deep learning is used.

Further, the feature amount calculated from the endoscopic image by the recognition processing unit 72 is preferably an index value obtained from a shape or a color of a predetermined portion of the observation target or an index value obtained from the shape and the color. For example, as the feature amount, preferably, at least one of a density of a blood vessel, a shape of a blood vessel, the number of branches of a blood vessel, a thickness of a blood vessel, a length of a blood vessel, a tortuosity of a blood vessel, a reaching depth of a blood vessel, a shape of a duct, a shape of an opening of a duct, a length of a duct, a tortuosity of a duct, or color information, or a value obtained by combining two or more of these values is used.

In FIG. 6 and FIG. 7, the recognition result correction unit 73 performs recognition result correction processing of correcting a recognition processing result obtained by the recognition processing unit 72. Hereinafter, the recognition result correction processing will be described. In the following description, the endoscopic image obtained from the recognition processing result on which the recognition result correction processing is to be performed is referred to as a specific image 80 (specific medical image (first medical image)) (FIG. 8).

Figure 8:
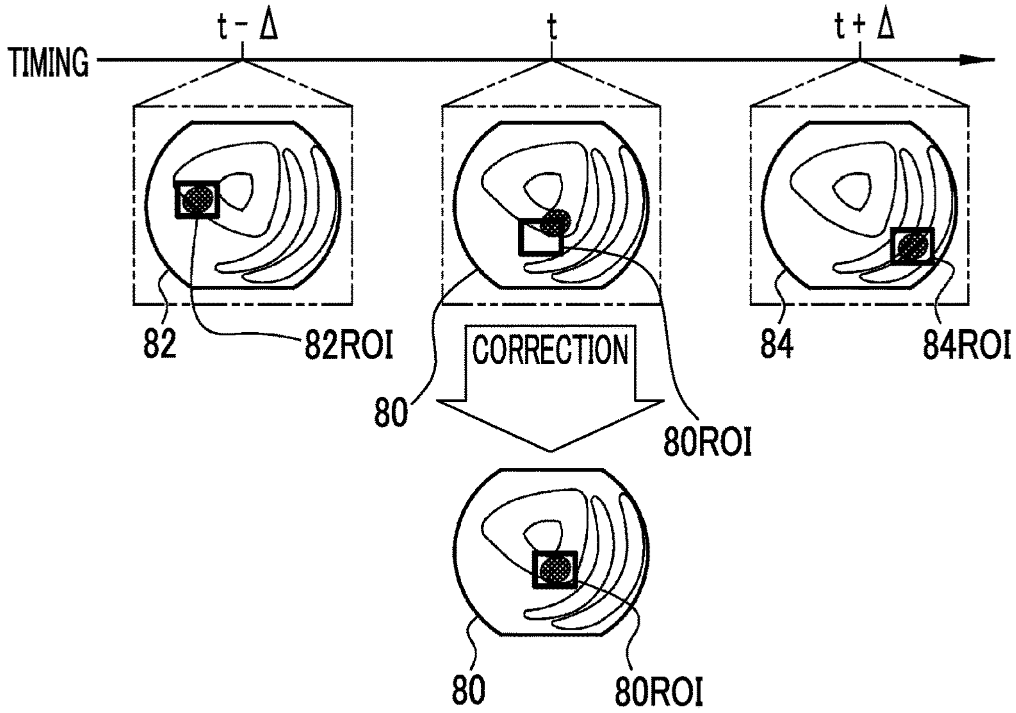
FIG. 8 is an explanatory diagram of recognition result correction processing.

As illustrated in FIG. 8, in the recognition result correction processing, position information of a region-of-interest 80ROI of a specific image 80 is corrected by using position information of a region-of-interest 82ROI of a previous image 82 (medical image for comparison (second medical image)) acquired (imaged) before the specific image 80 and position information of a region-of-interest 84ROI of a subsequent image 84 (medical image for comparison (second medical image)) acquired (imaged) after the specific image 80.

In a case where it is assumed that "t" is a timing when the specific image 80 is acquired (imaged), the previous image 82 is an endoscopic image acquired (imaged) at a timing "t−Δ". A value of "Δ" can be set as appropriate. In the present embodiment, the value of "Δ" is set such that the image acquired (imaged) immediately before the specific image 80 is the previous image 82. That is, for example, in a case where an endoscopic image is acquired by imaging the observation target at a cycle of 60 times (frames) per second, "Δ" is set to "1/60 (second)".

In a case where it is assumed that "t" is a timing when the specific image 80 is acquired (imaged), the subsequent image 84 is an endoscopic image acquired (imaged) at a timing "t+Δ". A value of "Δ" can be set as appropriate. In the present embodiment, the value of "Δ" is set such that the image acquired (imaged) immediately after the specific image 80 is the subsequent image 84. That is, for example, in a case where an endoscopic image is acquired by imaging the observation target at a cycle of 60 times (frames) per second, "Δ" is set to "1/60 (second)".

In the recognition result correction processing, the position (position information) of the region-of-interest 80ROI of the specific image 80 is changed (corrected) such that an intermediate position between the center of the region-of-interest 82ROI of the previous image 82 and the center of the region-of-interest 84ROI of the subsequent image 84 matches with the center of the region-of-interest 80ROI of the specific image 80. That is, the position information of the region-of-interest 80ROI of the specific image 80 is corrected by using a linear sum of pieces of the position information of the region-of-interest 82ROI of the previous image 82 and the region-of-interest 84ROI and the subsequent image 84.

Returning to FIG. 2, the normal image generated by the normal mode image processing unit 60, the special image generated by the special mode image processing unit 62, and the processing results obtained by the region-of-interest mode image processing unit 64 (the result of the recognition processing and the result of the recognition result correction processing) are input to the display control unit 58. The display control unit 58 generates a display screen using the input information, and outputs and displays the display screen on the monitor 18. The normal image, the special image, and the processing results may be stored in the memory 48 or the like instead of or in addition to being output and displayed on the monitor 18.

As described above, in the first embodiment, the recognition processing result of the specific image 80 is corrected by using the recognition processing result of the previous image 82 and the recognition processing result of the subsequent image 84, without changing the feature amount used for the recognition processing and/or a processing algorithm of the recognition processing or performing re-recognition processing after such a change. Thereby, it is possible to obtain a more accurate recognition processing result while reducing a processing load as compared with a case where the feature amount used for the recognition processing and/or the algorithm of the recognition processing is changed or re-recognition processing is performed.

In the first embodiment, in the recognition result correction processing, the position (center position) of the region-of-interest 80ROI of the specific image 80 is changed (refer to FIG. 8). On the other hand, a size of the region-of-interest 80ROI of the specific image 80 may be changed. In this case, the size of the region-of-interest 80ROI of the specific image 80 may be changed (enlarged or reduced) to a size (area) obtained by averaging a size (area) of the region-of-interest 82ROI of the previous image 82 and a size (area) of the region-of-interest 84ROI of the subsequent image 84.

Further, the size and the center position of the region-of-interest 80ROI may be changed such that an intermediate position between an upper right corner of the region-of-interest 82ROI of the previous image 82 and an upper right corner of the region-of-interest 84ROI of the subsequent image 84 is an upper right corner of the region-of-interest 80ROI of the specific image 80, that an intermediate position between a lower right corner of the region-of-interest 82ROI and a lower right corner of the region-of-interest 84ROI is a lower right corner of the region-of-interest 80ROI, that an intermediate position between an upper left corner of the region-of-interest 82ROI and an upper left corner of the region-of-interest 84ROI is an upper left corner of the region-of-interest 80ROI, and that an intermediate position between a lower left corner of the region-of-interest 82ROI and a lower left corner of the region-of-interest 84ROI is a lower left corner of the region-of-interest 80ROI. As described above, by correcting the size of the region-of-interest 80ROI, it is possible to obtain a more accurate recognition processing result.

In some cases, a lesion portion that does not exist in the specific image 80 may exist in the medical images for comparison (in the first embodiment, the previous image 82 and the subsequent image 84). Even in a case where the recognition processing result of the specific image 80 is corrected using the medical images for comparison, appropriate correction cannot be performed. Thus, it is preferable to correct the recognition result of the specific image 80 by using only the medical image for comparison in which the position of the region-of-interest is within a predetermined range from the position of the region-of-interest 80ROI of the specific image 80. By performing appropriate correction in this way, it is possible to obtain a more accurate recognition processing result.

Second Embodiment

In the first embodiment, an example of correcting the position information of the region-of-interest 80ROI of the specific image 80 in the recognition processing result correction processing has been described. On the other hand, the determination result of the specific image 80 may be corrected in the recognition processing result correction processing. In this case, the recognition processing unit 72 detects a lesion portion from the specific image 80 as in the first embodiment, and further performs determination processing of determining a type of a lesion from the detected lesion portion or performs determination processing on the entire specific image 80. The recognition result correction unit 73 corrects the determination result of the specific image 80 by using the determination result of the previous image 82 and the determination result of the subsequent image 84.

Figure 9:
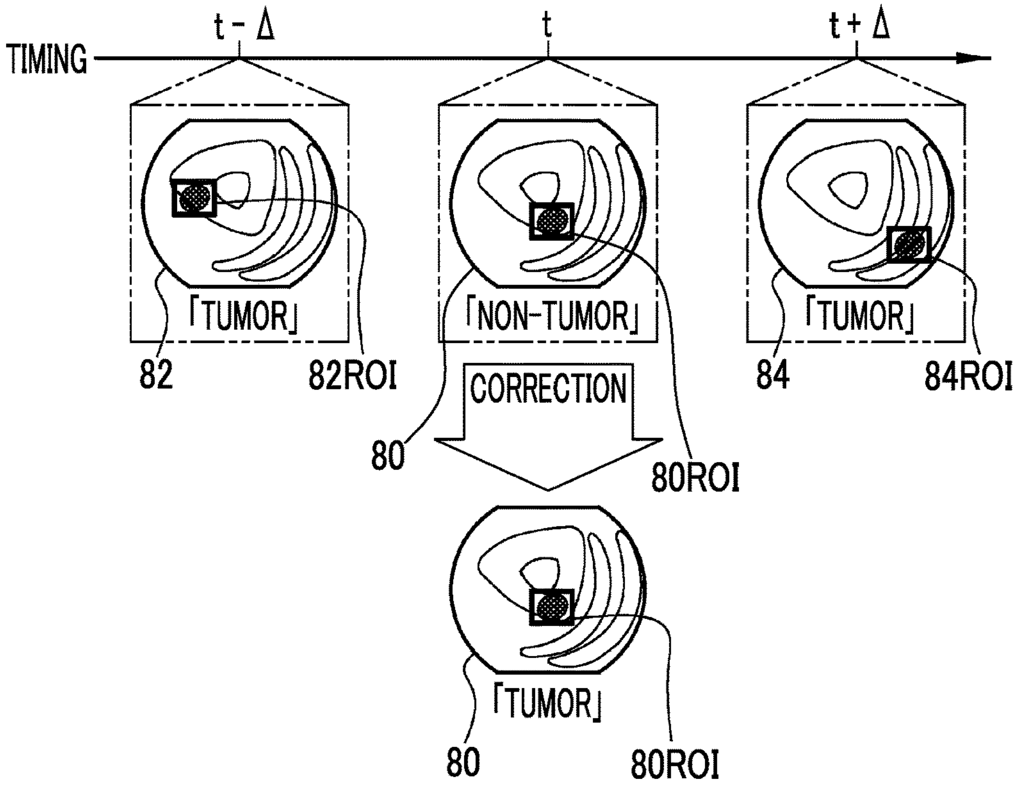
FIG. 9 is an explanatory diagram of recognition result correction processing.

Specifically, as illustrated in FIG. 9, in a case where the determination result of the region-of-interest 82ROI of the previous image 82 is "tumor", where the determination result of the region-of-interest 80ROI of the specific image 80 is "non-tumor", and where the determination result of the region-of-interest 84ROI of the subsequent image 84 is "tumor", the determination result of the region-of-interest 80ROI of the specific image 80 is changed (corrected) to "tumor". That is, the determination result of the specific image 80 is corrected to a determination result, which corresponds to the determination results of which the number is largest out of the number of the determination results of the previous images 82 and the subsequent images 84 for each type (the determination result of the specific image 80 is corrected by using the number of the determination results of the medical images for comparison for each type).

As a method for the determination processing by the recognition processing unit 72, preferably, artificial intelligence (AI), deep learning, convolutional neural network, template matching, texture analysis, frequency analysis, or the like is used.

Third Embodiment

In the above embodiment, the recognition processing result of the specific image 80 is corrected by using the recognition processing result of one previous image 82 and the recognition processing result of one subsequent image 84. On the other hand, the present invention is not limited thereto. For example, as illustrated in FIG. 10 and FIG. 11, the recognition processing result of the specific image 80 may be corrected by using recognition processing results of a plurality of previous images 82 and recognition processing results of a plurality of subsequent images 84.

Figure 10:
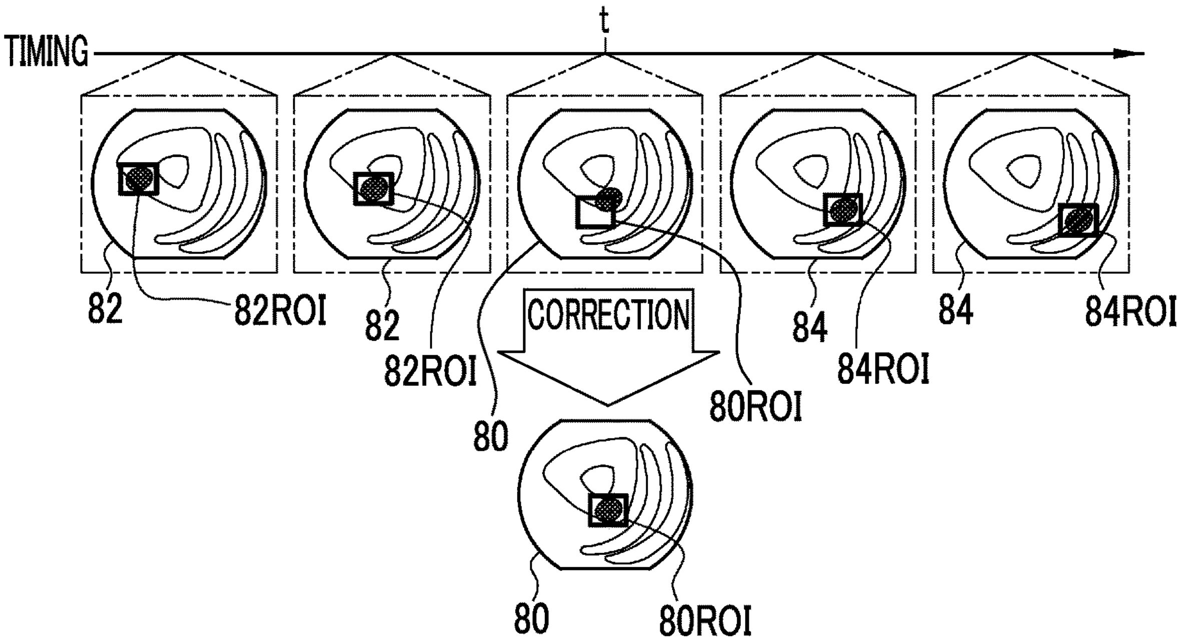
FIG. 10 is an explanatory diagram of recognition result correction processing.
Figure 11:
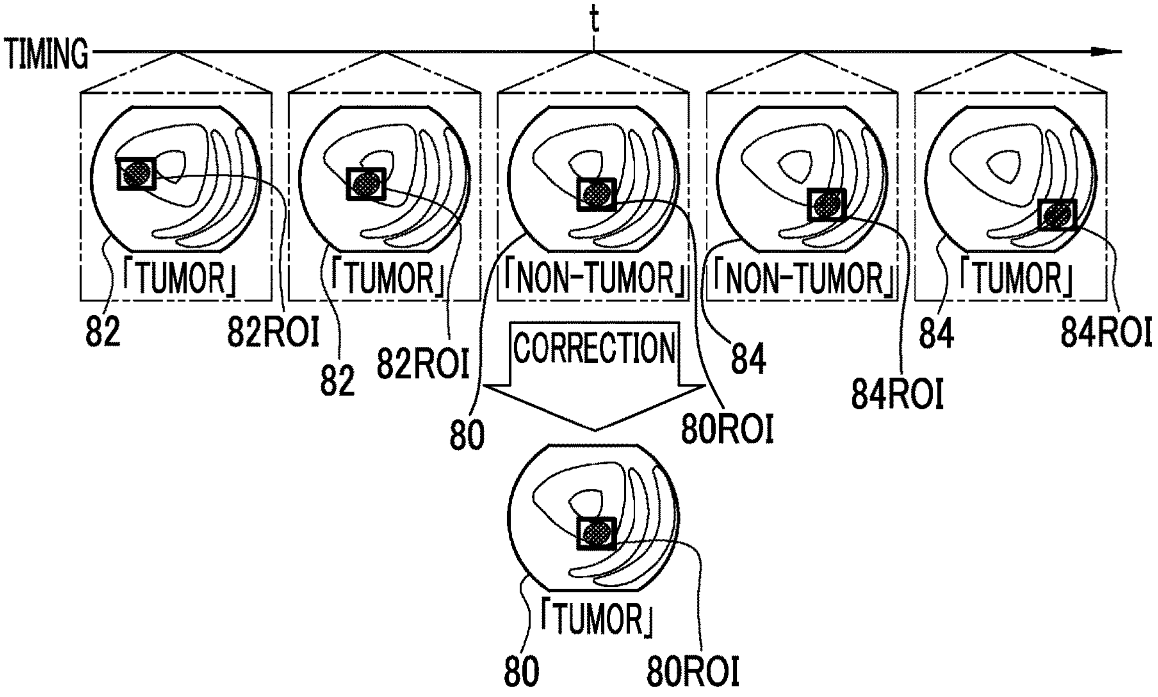
FIG. 11 is an explanatory diagram of recognition result correction processing.

In FIG. 10 and FIG. 11, the recognition processing result of the specific image 80 is corrected by using recognition processing results of two previous images 82 and recognition processing results of two subsequent images 84. Specifically, in FIG. 10, an average position between the center position of the regions-of-interest 82ROI of the two previous images 82 and the center position of the regions-of-interest 84ROI of the two subsequent images 84 is calculated, and the center position of the region-of-interest 80ROI of the specific image 80 is corrected such that the calculated position is the center position of the region-of-interest 80ROI. Further, in FIG. 11, the determination result of the specific image 80 is corrected to "tumor", which corresponds to the determination results of which the number for each type is largest out of the determination results of the two previous images 82 and the determination results of the two subsequent images 84. The recognition processing result of the specific image 80 may be corrected by using three or more previous images 82 and three or more subsequent images 84.

Further, the recognition processing result of the specific image 80 is corrected by using both the previous image 82 and the subsequent image 84. On the other hand, the recognition processing result of the specific image 80 may be corrected by using only one of the previous image 82 and the subsequent image 84. For example, in FIG. 10, in a case where the recognition result of the specific image 80 is corrected by using only the previous image 82, a movement amount and a movement direction per unit time of the center of the region-of-interest 82ROI may be calculated by comparing two previous images 82, and the position of the center of the region-of-interest 80ROI of the specific image 80 may be corrected by using the calculated movement amount and the calculated movement direction. Further, in FIG. 11, in a case where the recognition result of the specific image 80 is corrected by using only the previous image 82, the determination result of the specific image 80 may be corrected to the determination result of which the type is most out of types of the determination results of the two previous images 82.

Fourth Embodiment

In the embodiment described above, an example of performing the recognition processing and the recognition result correction processing on all the endoscopic images acquired by the region-of-interest mode image processing unit 64 has been described. On the other hand, the present invention is not limited thereto. For example, the recognition processing and the recognition result correction processing may be performed at predetermined time intervals or at predetermined frame intervals.

Figure 12:
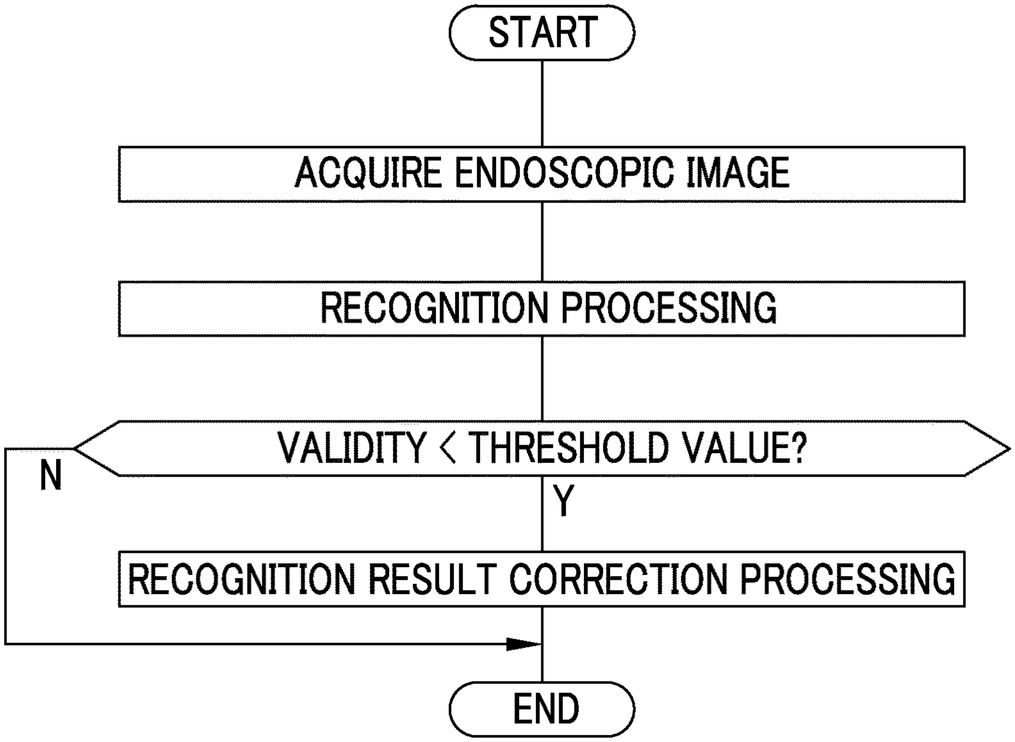
FIG. 12 is a flowchart illustrating a series of flows of a region-of-interest mode.

Further, as illustrated in FIG. 12, in a case where validity of the recognition processing result is lower than a predetermined threshold value, the recognition result correction processing may be performed. In this case, the recognition processing unit 72 executes recognition processing, calculates validity of the executed recognition processing, and notifies the recognition result correction unit 73 of the calculated validity. The recognition result correction unit 73 performs recognition result correction processing in a case where the validity of the recognition processing result is lower than a predetermined threshold value.

Figure 13:
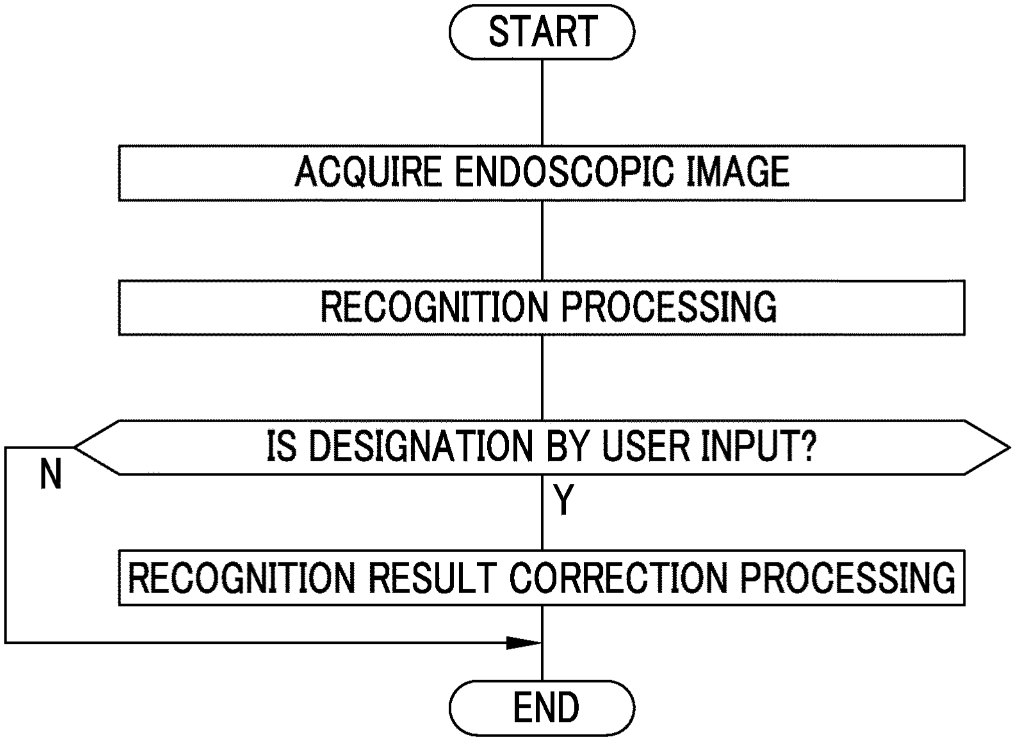
FIG. 13 is a flowchart illustrating a series of flows of a region-of-interest mode.

Further, as illustrated in FIG. 13, the recognition processing result may be corrected in a case where a designation by a user is input. In this case, the endoscopic image acquired by the region-of-interest mode image processing unit 64 or the recognition processing result obtained by the recognition processing unit 72 is displayed on the monitor 18. The user may designate a target (an endoscopic image or a recognition processing result) on which recognition result correction processing is to be performed by operating the console 19 while observing the monitor 18. Further, in a case where the still image acquisition unit 13*b* is operated, it is considered that a designation by a user is input, and the recognition result correction processing may be performed on the endoscopic image acquired by the operation of the still image acquisition unit 13*b*. In a case where the recognition processing result correction processing is performed according to the designation by the user, a result of recognition processing of the previous image 82 and/or the subsequent image 84 is required for the recognition processing result correction processing. Therefore, recognition processing on the endoscopic image other than the processing may be omitted.

Fifth Embodiment

Figure 14:
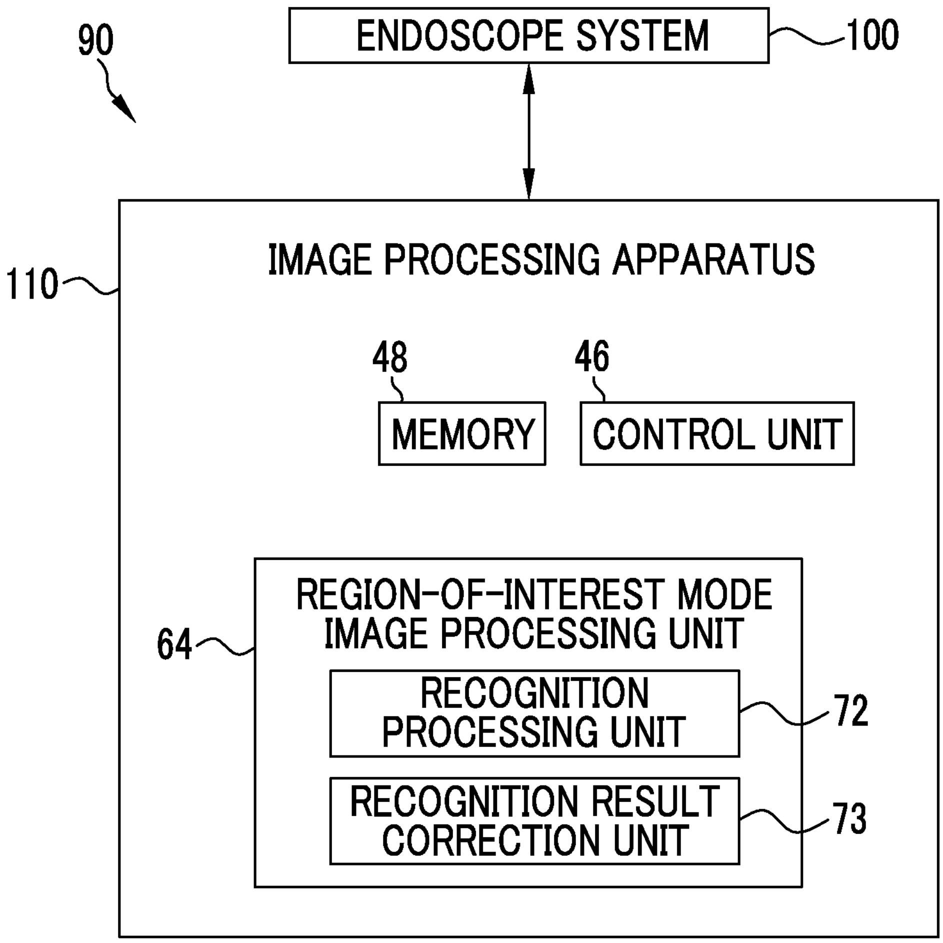
FIG. 14 is a block diagram illustrating a function of an image processing apparatus.

In the embodiment described above, an example in which the processor device 16 as a part of the endoscope system 10 functions as a processor according to the present invention, that is, an example in which the control unit 46 as a processor according to the present invention is incorporated in the endoscope system 10 (processor device 16) and the endoscope system 10 (processor device 16) functions as the region-of-interest mode image processing unit 64 has been described. On the other hand, the present invention is not limited thereto. As in a medical image processing system 90 illustrated in FIG. 14, an image processing apparatus 110 may be provided separately from the endoscope system 100, and a control unit 46 and a memory 48 may be provided in the image processing apparatus 110. In this case, the image processing apparatus 110 may be configured to function as the region-of-interest mode image processing unit 64. In FIG. 14, the image processing apparatus 110 is connected to the endoscope system 100, and an endoscopic image is transmitted from the endoscope system 100 to the image processing apparatus 110. In the image processing apparatus 110, the region-of-interest mode image processing unit 64 performs recognition processing and recognition result correction processing, and transmits results of recognition processing and recognition result correction processing to a predetermined notification destination (in the example of FIG. 14, the endoscope system 100).

Of course, the image processing apparatus 110 described above may be connected to an apparatus or a system that acquires a medical image other than the endoscopic image, and may be configured as a medical image processing system that performs recognition processing and recognition result correction processing on the medical image other than the endoscopic image. Examples of the medical image other than the endoscopic image include an ultrasound image obtained by an ultrasound diagnostic apparatus, an X-ray image obtained by an X-ray inspection apparatus, a computed tomography (CT) image obtained by a CT inspection apparatus, a magnetic resonance imaging (MRI) inspection image obtained by an MRI inspection apparatus, and the like.

The control unit 46 (processor) according to the present invention includes a central processing unit (CPU) which is a general-purpose processor that functions as various processing units such as the region-of-interest mode image processing unit 64, a graphical processing unit (GPU), a field programmable gate array (FPGA), and the like. The control unit 46 (processor) according to the present invention includes a dedicated electric circuit which is a processor having a circuit configuration specifically designed to execute various processing, and the like, in addition to a CPU, a GPU, and a programmable logic device (PLD) such as an FPGA which is a processor capable of changing a circuit configuration after manufacture.

One processing unit may be configured by one of these various processors, or may be configured by a combination of two or more processors having the same type or different types (for example, a combination of a plurality of FPGAs, a combination of a CPU and an FPGA, a combination of a CPU and a GPU, or the like). Further, the plurality of processing units may be configured by one processor. As an example in which the plurality of processing units are configured by one processor, firstly, as represented by a computer such as a client and a server, a form in which one processor is configured by a combination of one or more CPUs and software and the processor functions as the plurality of processing units is adopted. Secondly, as represented by a system on chip (SoC) or the like, a form in which a processor that realizes the function of the entire system including the plurality of processing units by one integrated circuit (IC) chip is used is adopted. As described above, the various processing units are configured by using one or more various processors as a hardware structure.

Further, as the hardware structure of the various processors, more specifically, an electric circuit (circuitry) in which circuit elements such as semiconductor elements are combined is used.

EXPLANATION OF REFERENCES

10: endoscope system (medical image processing system)
12: endoscope
12*a*: insertion part
12*b*: operating part
12*c*: bendable part
12*d*: tip part
13*a*: angle knob
13*b*: still image acquisition unit
13*c*: mode switching unit
13*d*: zoom operating part
14: light source device
16: processor device
18: monitor
19: console
20: light source unit
20*a*: V-LED
20*b*: B-LED
20*c*: G-LED
20*d*: R-LED
22: light source control unit
23: wavelength cut filter
24: light guide
30*a*: Illumination optical system
30*b*: imaging optical system
32: Illumination lens
34: objective lens
36: magnification optical system
36*a*: zoom lens
36*b*: lens drive unit
38: imaging sensor
40: CDS circuit
42: AGC circuit
44: A/D conversion circuit
46: control unit (processor)
48: memory
50: image signal acquisition unit
52: DSP
54: noise reduction unit
56: image processing unit
58: display control unit
60: normal mode image processing unit

62: special mode image processing unit
64: region-of-interest mode image processing unit
72: recognition processing unit
73: recognition result correction unit
80: specific image (specific medical image)
80ROI: region-of-interest
82: previous image (medical image for comparison)
82ROI: region-of-interest
84: subsequent image (medical image for comparison)
84ROI: region-of-interest
90: medical image processing system
100: endoscope system
110: image processing apparatus

What is claimed is:

1. A medical image processing system comprising:

a memory that stores a program instruction; and a processor configured to execute the program instruction, wherein the processor is configured to:

sequentially acquire a plurality of medical images generated by continuously imaging an observation target;

detect regions-of-interest from the medical images by performing recognition processing on each of the plurality of medical images; and correct position information of the region-of-interest detected by the recognition processing performed on a first medical image among the plurality of medical images by using pieces of position information of the regions-of-interest detected by the recognition processing performed on second medical images which are different from the first medical image among the plurality of medical images, wherein the second medical images include an image which is imaged before capturing the first medical image, and wherein in the correction, the position of the region-of-interest of the first medical image is corrected such that an intermediate position of the center positions of the region-of-interest among the plurality of second medical images matches with the center of the region-of-interest of the first medical image.

2. The medical image processing system according to claim 1, wherein the correction is performed in a case where validity of a result of the recognition processing performed on the first medical image is lower than a predetermined threshold value.

3. The medical image processing system according to claim 1, wherein the correction is performed in a case where an instruction by a user is input.

4. The medical image processing system according to claim 1, wherein the recognition processing includes determination processing of determining the region-of-interest.

5. The medical image processing system according to claim 4, wherein, in the correction, correction of a result of the determination is performed.

6. The medical image processing system according to claim 1, wherein, in the recognition processing, a convolutional neural network is used.

7. The medical image processing system according to claim 1, wherein, in the recognition processing, a lesion portion is detected as the regions-of-interest.

8. The medical image processing system according to claim 1, wherein the medical image is an image obtained from an endoscope.

9. A medical image processing system comprising:

a memory that stores a program instruction; and a processor configured to execute the program instruction, wherein the processor is configured to:

sequentially acquire a plurality of medical images generated by continuously imaging an observation target;

detect regions-of-interest from the medical images by performing recognition processing on each of the plurality of medical images; and correct position information of the region-of-interest detected by the recognition processing performed on a first medical image among the plurality of medical images by using pieces of position information of the regions-of-interest detected by the recognition processing performed on second medical images which are different from the first medical image among the plurality of medical images, wherein the second medical images include an image which is imaged after capturing the first medical image, and wherein in the correction, the position of the region-of-interest of the first medical image is corrected such that an intermediate position of the center positions of the region-of-interest among the plurality of second medical images matches with the center of the region-of-interest of the first medical image.

10. The medical image processing system according to claim 9, wherein the correction is performed in a case where validity of a result of the recognition processing performed on the first medical image is lower than a predetermined threshold value.

11. A medical image processing system comprising:

a memory that stores a program instruction; and a processor configured to execute the program instruction, wherein the processor is configured to:

sequentially acquire a plurality of medical images generated by continuously imaging an observation target;

detect regions-of-interest from the medical images by performing recognition processing on each of the plurality of medical images; and correct position information of the region-of-interest detected by the recognition processing performed on a first medical image among the plurality of medical images by using pieces of position information of the regions-of-interest detected by the recognition processing performed on second medical images which are different from the first medical image among the plurality of medical images, wherein the second medical images include images which are imaged before and after capturing the first medical image, and wherein in the correction, the position of the region-of-interest of the first medical image is corrected such that an intermediate position of the center positions of the region-of-interest among the plurality of second medical images matches with the center of the region-of-interest of the first medical image.

12. The medical image processing system according to claim 11, wherein the correction is performed in a case where validity of a result of the recognition processing performed on the first medical image is lower than a predetermined threshold value.

13. A medical image processing system comprising:

a memory that stores a program instruction; and a processor configured to execute the program instruction, wherein the processor is configured to:

sequentially acquire a plurality of medical images generated by continuously imaging an observation target;

detect regions-of-interest from the medical images by performing recognition processing on each of the plurality of medical images; and correct position information of the region-of-interest detected by the recognition processing performed on a first medical image among the plurality of medical images by using pieces of position information of the regions-of-interest detected by the recognition processing performed on second medical images which are different from the first medical image among the plurality of medical images, wherein the second medical images include images which are imaged before and/or after capturing the first medical image, and wherein, in the correction, a linear sum of the pieces of position information of the regions-of-interest of the second medical images is used.

14. A medical image processing system comprising:

a memory that stores a program instruction; and a processor configured to execute the program instruction, wherein the processor is configured to:

sequentially acquire a plurality of medical images generated by continuously imaging an observation target;

detect regions-of-interest from the medical images by performing recognition processing on each of the plurality of medical images; and correct position information of the region-of-interest detected by the recognition processing performed on a first medical image among the plurality of medical images by using pieces of position information of the regions-of-interest detected by the recognition processing performed on second medical images which are different from the first medical image among the plurality of medical images, wherein the second medical images include images which are imaged before and/or after capturing the first medical image, and wherein, in the correction, the position information of the region-of-interest which is located within a predetermined range from the region-of-interest of the first medical image among the regions-of-interest of the second medical images is used.

15. A medical image processing system comprising:

a memory that stores a program instruction; and a processor configured to execute the program instruction, wherein the processor is configured to:

sequentially acquire a plurality of medical images generated by continuously imaging an observation target;

detect regions-of-interest from the medical images by performing recognition processing on each of the plurality of medical images; and correct position information of the region-of-interest detected by the recognition processing performed on a first medical image among the plurality of medical images by using pieces of position information of the regions-of-interest detected by the recognition processing performed on second medical images which are different from the first medical image among the plurality of medical images, wherein the second medical images include images which are imaged before and/or after capturing the first medical image, wherein the recognition processing includes determination processing of determining the region-of-interest, wherein, in the correction, correction of a result of the determination is performed, and wherein, in the correction of the result of the determination, the number of the result of the determination of the second medical images for each type is used.

16. A medical image processing system comprising:

a memory that stores a program instruction; and a processor configured to execute the program instruction, wherein the processor is configured to:

sequentially acquire a plurality of medical images generated by continuously imaging an observation target;

detect regions-of-interest from the medical images by performing recognition processing on each of the plurality of medical images; and correct position information of the region-of-interest detected by the recognition processing performed on a first medical image among the plurality of medical images by using pieces of position information of the regions-of-interest detected by the recognition processing performed on second medical images which are different from the first medical image among the plurality of medical images, wherein the second medical images include images which are imaged before and/or after capturing the first medical image, and wherein in the correction, the size of the region-of-interest of the first medical image is changed to a size obtained by averaging a size of the region-of-interest of the plurality of second medical images.

* * * * *